US008404704B2

(12) United States Patent
Viscomi et al.

(10) Patent No.: US 8,404,704 B2
(45) Date of Patent: *Mar. 26, 2013

(54) USE OF POLYMORPHIC FORMS OF RIFAXIMIN FOR MEDICAL PREPARATIONS

(75) Inventors: Giuseppe Claudio Viscomi, Bologna (IT); Manuela Campana, Bologna (IT); Donatella Confortini, Bologna (IT); Miriam Barbanti, Bologna (IT); Fiorella Calanni, Bologna (IT)

(73) Assignee: Alfa Wassermann S.p.A., Alanno (PE) (IT)

( * ) Notice: Subject to any disclaimer, the term of this patent is extended or adjusted under 35 U.S.C. 154(b) by 0 days.

This patent is subject to a terminal disclaimer.

(21) Appl. No.: 13/041,348

(22) Filed: Mar. 4, 2011

(65) Prior Publication Data
US 2012/0059023 A1 Mar. 8, 2012

Related U.S. Application Data

(63) Continuation of application No. 11/873,841, filed on Oct. 17, 2007, now Pat. No. 7,915,275, which is a continuation-in-part of application No. 11/135,651, filed on May 24, 2005, now abandoned, which is a continuation-in-part of application No. PCT/EP2004/012490, filed on Nov. 4, 2004.

(30) Foreign Application Priority Data

Nov. 7, 2003 (IT) .............................. MI2003A2144

(51) Int. Cl.
*A61K 31/395* (2006.01)
(52) U.S. Cl. ...................................................... 514/279
(58) Field of Classification Search .................... 514/279
See application file for complete search history.

(56) References Cited

U.S. PATENT DOCUMENTS

| 4,341,785 A | 7/1982 | Marchi et al. |
| 4,557,866 A | 12/1985 | Cannata et al. |
| 7,045,620 B2 | 5/2006 | Viscomi et al. |
| 2009/0028940 A1 | 1/2009 | Jahagirdar et al. |
| 2009/0082558 A1 | 3/2009 | Kothakonda et al. |
| 2009/0312357 A1 | 12/2009 | Rao et al. |

FOREIGN PATENT DOCUMENTS

| CA | 1215976 | 12/1986 |
| CA | 1218650 | 3/1987 |
| EP | 0161534 A2 | 11/1985 |
| EP | 1698630 A1 | 9/2006 |
| EP | 1557421 B1 | 5/2007 |
| EP | 2011486 A1 | 1/2009 |
| IT | MI2005A000345 | 3/2005 |
| WO | 2008/155728 A1 | 12/2008 |
| WO | 2009/08005 A1 | 1/2009 |
| WO | 2009/047801 A1 | 4/2009 |
| WO | 2009/108730 A2 | 9/2009 |

OTHER PUBLICATIONS

European Patent No. 1 557 421, Reply to the Communication pursuant to Article 96(2), May 2, 2006. (D2).
European Patent No. 1 557 421, Opposition Proceedings, "Notice of opposition to a European patent," Feb. 11, 2008.
European Patent No. 1 557 421, Opposition Proceedings, Patentee response to Notice of Opposition, Sep. 10, 2008.
European Patent No. 1 557 421, Opposition Proceedings, Opinion of the Opposition Division, Jan. 19, 2009.
European Patent No. 1 557 421, Opposition Proceedings, Patentee response to summons to attend oral proceedings, Apr. 22, 2009.
European Patent No. 1 557 421, Opposition Proceedings, Opponent response to summons to attend oral proceedings, Apr. 29, 2009.
European Patent No. 1 557 421, Opposition Proceedings, Patentee response to brief communication, May 29, 2009.
European Patent No. 1 557 421, Opposition Proceedings, European Patent Office Decision rejecting the opposition, Jul. 8, 2009.
European Patent No. 1 557 421, Opposition Proceedings, Appellant Notice of Appeal, Sep. 18, 2009.
European Patent No. 1 557 421, Opposition Proceedings, Appellant Statement of Grounds for Appeal, Nov. 18, 2009.
Alvisi, V. et al., "Treatment of Secretory Diarrhoeas—A Double-Blind Trial of the Effectiveness of Rifaximin (L 105) and Neomycin," Clinical Trials Journal, 1984, 21, No. 4, pp. 215-223.
Rodriguez-Spong, B. et al., "General Principles of Pharmaceutical Solid Polymorphism: a Supramolecular Perspective," Advanced Drug Delivery Reviews, 56 (2004), 241-274.
Morris, K.R. et al., "Theoretical Approaches to Physical Transformations of Active Pharmaceutical Ingredients During Manufacturing Processes," Advanced Drug Delivery Reviews, 48 (2001), 91-114.
Viscomi, G.C. et al., "Crystal Forms of Rifaximin and Their Effect on Pharmaceutical Properties," CrysEngComm, 2008, 10, 1074-1081.
Brufani, M. et al., "X-Ray Crystal Structure of 4-Deoxy-3'-bromopyrido[1',2'-1,2]imidazo[5,4-c]rifamycin S," The Journal of Antibiotics, 37:12, 1623-1627 (Dec. 1984).
Soro, O. et al., "Selection of Rifampicin-Resistant Mycobacterium Tuberculosis Does Not Occur in the Presence of Low Concentrations of Rifaximin," Clin Microbiol Infect, 1997, 3:147-151.
TicinumLab. Example 7, Patent EP 0 161 534, "Synthesis of 4-Deoxy-4'methyl-pyrido-[1',2':1,2 ]imidazo]5,4-c]ryfamicin Sv," (2009).
TicinumLab. Example 9, Patent EP 0 161 534, "Synthesis of 4-Deoxy-4'methyl-pyrido-[1',2':1,2]imidazo]5,4-c]ryfamicin SV," (2009).
Department of Health and Human Services, Certificate of GMP Compliance of a Manufacturer, Nov. 16, 2007.
European Medicines Industry, ICH Topic Q6A, Specifications: Test Procedures and Acceptance Criteria for New Drug Substances and New Drug Products: Chemical Substances, pp. 1-32, 2000.

(Continued)

*Primary Examiner* — Bruck Kifle
(74) *Attorney, Agent, or Firm* — Kenneth H. Sonnenfeld; King & Spalding

(57) ABSTRACT

The present invention relates to Rifaximin polymorphic forms α, β and γ, to their use in medicinal preparations for the oral or topical route and to therapeutic methods using them.

15 Claims, 9 Drawing Sheets

OTHER PUBLICATIONS

Henwood, S.Q. et al., "Solubility and Dissolution Properties of Generic Rifampicin Raw Materials," Drug Development and Industrial Pharmacy, 26(4), 403-408 (2000).

Morris, K.R. "Polymorphism in Pharmaceutical Solids," in "Structural Aspects of Hydrates and Sovates," H.G. Brittain editor, Drugs and the Pharmaceutical Sciences, vol. 95, Chapter 4, pp. 125-181, 1999.

Rifaximin—Intrinsic Dissolution Experimental Data, Apr. 2009.

Bacchi, A. et al., "Sampling Rifamycin Conformational Variety by Cruising Through Crystal Forms: Implications for Polymorph Screening and for Biological Models," New J. Chem., 2008, 32, 1725-1735.

Venturini, A.P. "Pharmacokinetics of L/105, a New Rifamycin, in Rats and Dogs, after Oral Administration," Chemotherapy 29:1-3 (1983).

Pelizza, G. "Polymorphism of Rifampicin," II Farmaco—Ed. Sc., vol. 32, No. 7, pp. 471-481, 1977.

Rao, R.N. et al., "O-Line 2D-LC-ESI/MS/MS Determination of Rifaximin in Rat Serum," Biomed. Chromatogr. 2009, 1-6.

Descombe, J.J. et al., "Pharmacokinetic Study of Rifaximin After Oral Administration in Healthy Volunteers," Int. J. Clin. Pharm. Res. XIV(2), 51-56 (1994).

Rossi, C. et al., "NMR Investigation of a New Semisynthetic Bioactive Compound," Bulletin of Magnetic Resonance, 1996, vol. 18, No. 1-2, pp. 87-90.

Italian Product Label for Normix (rifaximin), Apr. 23, 1985.

Cellai, L. et al., "A Study of Structure-Activity Relationships in 4-Deoxypyrido[1',2'-1,2] imidazo[5,4-c]rifamycin SV Derivatives by Electron Spectroscopy for Chemical Analysis and 1H NMR," Molecular Pharmacology, 27:103-108, 1984.

European Patent No. 1 557 421, Opposition Proceedings, "Opponent Response to the Late Submissions of Patentee," Jun. 11, 2009.

European Patent No. 1 557 421, Opposition Proceedings, "Patentee Response to Opponent Statement Setting Out the Grounds of Appeal," Jun. 2, 2010.

Zach Systems SPA, "Synthesis of rifaximin obtained according to examples 7 and 9 reported in European Patent EP0161534," May 13, 2010.

Figure 1 Dissolution profile of Form α and Form β within 0-22 hours
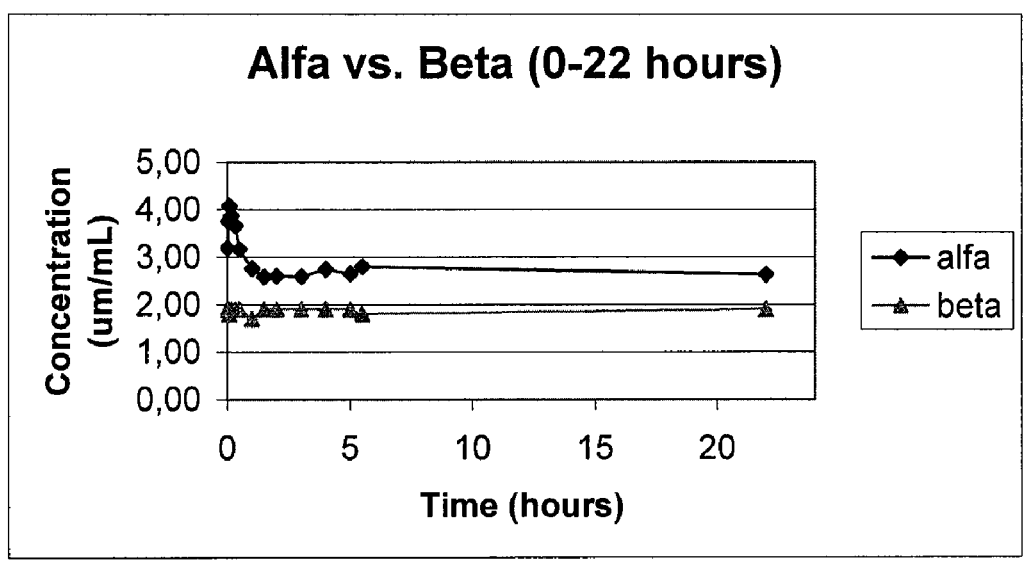

Figure 2 Dissolution profile of Form α and Form β within 0-96hours
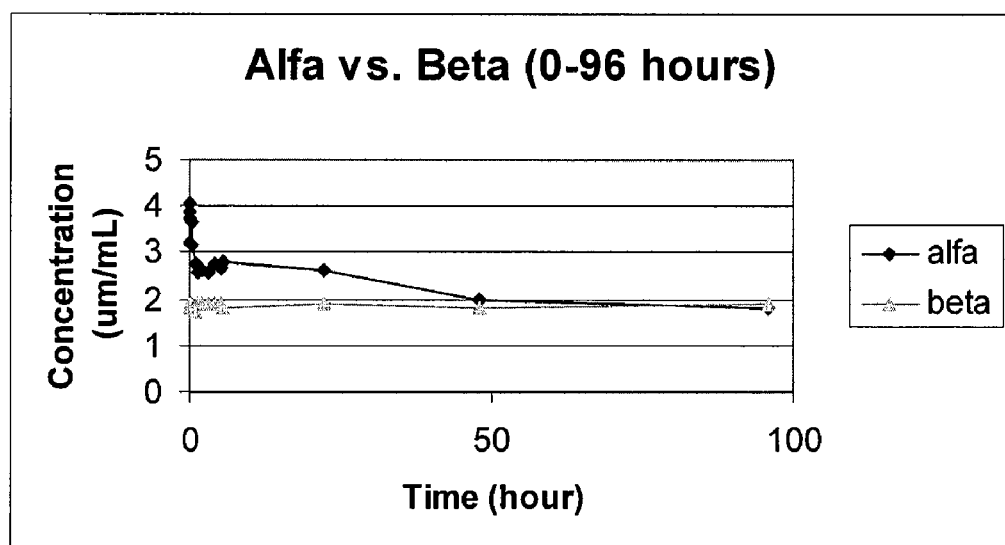

Figure 3 Dissolution profile of Form β and Form γ within 0-22 hours
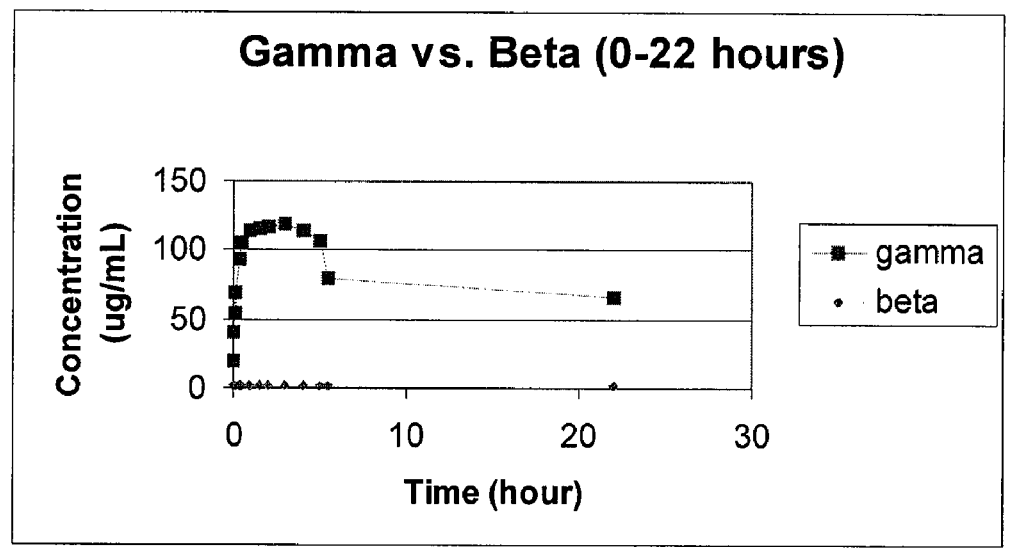

Figure 4 Dissolution profile of Form γ and Form β within 0-96 hours
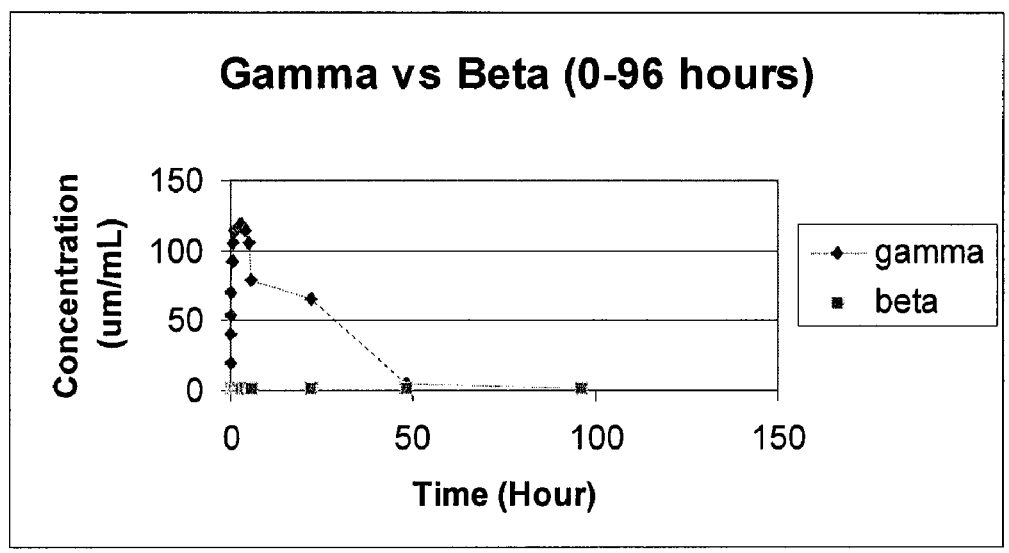

Figure 5 Table showing the data obtained from the dissolution profiles depicted in Figures 1-4

| Rifaximin Polymorphism | C max (ug/mL) | T max (min) | Conc. after 3 hours. (ug/ml) |
|---|---|---|---|
| | | | |
| Alfa | 4,07 | 5 | 2,5 |
| | | | |
| Beta | 1,9 | 0 | 1,9 |
| | | | |
| Gamma | 118 | 50-80 | 79 |

Figure 6 Intrinsic dissolution in 0.1 m aqueous phosphate buffer at pH 7.4 with 0.45 % sodium lauryl–sulphate

| Time (min) | Rifaximin dissolved (mg/cm$^2$) | |
|---|---|---|
| | β polymorph | γ polymorph |
| 15 | 0,28 | 2,46 |
| 30 | 0,50 | 4,52 |
| 45 | 0,72 | 6,44 |
| 60 | 0,94 | 9,04 |
| | | |
| Intrinsic dissolution rate (mg/min/cm$^2$) | 0,0147 | 0,1444 |

USE OF POLYMORPHIC FORMS OF RIFAXIMIN FOR MEDICAL PREPARATIONS

RELATED APPLICATIONS

This application is a continuation of U.S. application Ser. No. 11/873,841, filed on Oct. 17, 2007, which in turn is a continuation-in part of U.S. application Ser. No. 11/135,651, filed on May 24, 2005, now abandoned, which is a continuation-in-part of PCT/EP04/12490, filed on Nov. 4, 2004, which claims priority to Italian application No. MI2003A002144 filed Nov. 7, 2003, all of which are incorporated by reference herein in their entirety, including any drawings.

BACKGROUND

Rifaximin (INN; see The Merck Index, XIII Ed., 8304) is an antibiotic belonging to the rifamycin class of antibiotics, e.g., a pyrido-imidazo rifamycin. Rifaximin exerts its broad antibacterial activity, for example, in the gastrointestinal tract against localized gastrointestinal bacteria that cause infectious diarrhea, irritable bowel syndrome, small intestinal bacterial overgrowth, Crohn's disease, and/or pancreatic insufficiency. It has been reported that rifaximin is characterized by a negligible systemic absorption, due to its chemical and physical characteristics (Descombe J. J. et al. *Pharmacokinetic study of rifaximin after oral administration in healthy volunteers. Int J Clin Pharmacol Res*, 14 (2), 51-56, (1994)).

Rifaximin is described in Italian Patent IT 1154655 and EP 0161534, both of which are incorporated herein by reference in their entirety for all purposes. The EP patent discloses a process for rifaximin production using rifamycin O as the starting material (The Merck Index, XIII Ed., 8301). These patents generically describe purification strategies of rifaximin by crystallization in suitable solvents or solvent systems and summarily show in some examples that the resulting product can be crystallized from the 7:3 mixture of ethyl alcohol/water and dried both under atmospheric pressure and under vacuum. Neither patent discloses any experimental conditions, or further guidance for crystallization and drying or any indication that rifaximin exists in polymorphic forms. U.S. Pat. No. 7,045,620 B1 discloses the identification, characterization and process for obtaining polymorphic forms of rifaximin.

The identification and characterization of polymorphic forms, as well as the experimental conditions for obtaining polymorphs, is important for therapeutic compounds. Polymorphs of a compound can influence the pharmaco-toxicologic properties of the drug, such as bioavailability, solubility, stability, colour, compressibility, flowability and workability with consequent modification of the profiles of toxicological safety, clinical effectiveness and productive efficiency.

Rifaximin is approved for the treatment of pathologies caused by non-invasive strains as *Escherichia coli*, microorganism which are not able to penetrate into GI mucosa and they remain in contact with the GI fluids.

Since 1980, when discovered, rifaximin appeared to be a non-adsorbed antibiotic and the published data on the bioavailability of rifaximin indicate that the maximum plasma level of rifaximin after oral administration appeared to be almost negligible, being in the range from 2 and 5 ng/ml (Descombe J. J. et al. *Pharmacokinetic study of rifaximin after oral administration in healthy volunteers. Int J Clin Pharmacol Res*, 14 (2), 51-56, (1994)).

This was considered an intrinsic property of the compound and the pharmaceutical develop was designed on this property.

As far as the drug safety profile is concerned, it should be reminded that in the therapeutic practice, antibiotics may cause bacterial resistance to the same or other similar antibiotics. This is particularly relevant to rifaximin because it belongs to the rifamycin family along with rifampicin, which is the standard of care for the treatment of tuberculosis. The current short course treatment for tuberculosis is a combination therapy involving four active pharmaceutical ingredients: rifampicin, isoniazid, ethambutol and pyrazinamide, with rifampicin playing a pivotal role. Therefore, any drug which jeopardizes the efficacy of the therapy by selecting for resistance to rifampicin would be harmful. (Kremer L. et al. "*Re-emergence of tuberculosis: strategies and treatment*", *Expert Opin. Investig. Drugs*, 11 (2), 153-157, (2002)). Thus, it is possible that the use of rifaximin might induce the selection resistant strains of *M. tuberculosis* and cross-resistance to rifampicin. Polymorphic forms may provide a mechanism to avoid this negative event because the quantity of systemically absorbed rifaximin may be controllable through the use of polymorphic forms.

SUMMARY

It has now been unexpectedly found that polymorphic forms of rifaximin described in U.S. Pat. No. 7,045,620 B1, have different in vivo bioavailability properties and, therefore, are useful in the preparation of pharmaceuticals with different characteristics for the treatment of infections. Thus allowing one to generate rifaximin preparations that show significantly different levels of adsorption with $C_{max}$ values from about 0.0 ng/ml to 5.0 µg/ml. This also allows one to obtain rifaximin preparations ranging from being negligibly to significantly adsorbed forms. It was unexpectedly found that rifaximin polymorphic form is endowed with distinct pharmaceutical properties compared with what was known for rifaximin.

By the present invention it is possible to modulate the therapeutic action by selecting the proper polymorphic form.

In case of invasive bacteria, it may be useful to use the most bioavailable polymorphic form, whereas in case of non-invasive pathogens it may be more appropriate to use the less adsorbed forms, since they are safer.

Some features of polymorph α include, for example:
a water content (w/w) from about 0 to about 3.0%.
a $C_{max}$ of polymorph a from about 0.0 ng/ml to about 5.5 ng/ml.
a $t_{max}$ from about 1.0 h to about 6 h.
a $AUC_{0-24h}$ from about 0 to about 100 ng·h/ml.
a $AUC_{0-inf}$ from about 0 to 110 ng·h/ml.

Some features of polymorph β include, for example:
a water content from about 4.5 to about 100%.
a $C_{max}$ from about 0.0 to about 40 ng/ml.
a $t_{max}$ between about 1 and about 6 h
a $AUC_{0-24h}$ from about 0 to about 40 ng·h/ml.
a $AUC_{0-inf}$ from about 0 to about 45 ng·h/ml.
an intrinsic dissolution rate between about 0.001 and about 0.016 mg/min/cm².

Some features of polymorph γ include, for example:
a water content from about 0% to about 2%.
a $C_{max}$ from about 0.0 to about 5000 ng/ml.
a $t_{max}$ from about 1.0 h to about 6.0 h.
a $AUC_{0-24h}$ from about 0.0 to about 22000 ng·h/ml.
a $AUC_{0-inf}$ from about 0.0 to about 22000 ng·h/ml.

an intrinsic dissolution rate from about 0.1 to about 0.16 mg/min/cm$^2$.

In one aspect, a pharmaceutical composition is presented, which comprises one or more of a Form α, Form β, or Form γ polymorph of rifaximin and a pharmaceutically acceptable carrier.

In one embodiment, the pharmaceutical composition further comprises excipients.

According to another embodiment, the excipients are one or more of a diluting agent, binding agent, lubricating agent, disintegrating agent, colouring agent, flavouring agent or sweetening agent.

In another embodiment, the composition is formulated for selected coated and uncoated tablets, hard and soft gelatine capsules, sugar-coated pills, lozenges, wafer sheets, pellets and powders in sealed packet.

In one embodiment, the composition is formulated for topical use.

Presented herein, according to one aspect, are methods of treating, preventing, or alleviating a bowel related disorder comprising administering to a subject in need thereof a cell infected with a virus with an effective amount of one or more of a Form α, Form β, or Form γ polymorph of rifaximin.

According to another embodiment, wherein the bowel related disorder is one or more of irritable bowel syndrome, travelers' diarrhea, small intestinal bacterial overgrowth, Crohn's disease, chronic pancreatitis, pancreatic insufficiency, or colitis.

Presented herein, according to one aspect, are methods of assessing the efficacy of a bowel related disorder treatment in a subject, monitoring the progress of a subject being treated for a bowel related disorder, or a method of selecting a subject for treatment of a bowel disorder, comprising:

determining a pre-treatment level of bacterial overgrowth;

administering a therapeutically effective amount of one or more of a Form α, Form β, or Form γ polymorph of rifaximin to the subject; and determining a post-treatment level of bacterial overgrowth after an initial period of treatment with the one or more of Form α, Form β, or Form γ polymorph of rifaximin.

In one embodiment, the modulation of the level of bacterial overgrowth indicates efficacy of the treatment.

In another embodiment, a decrease in bacterial overgrowth indicates that the treatment is efficacious.

In another embodiment, the modulation of the bacterial overgrowth is an indication that the subject is likely to have a favourable clinical response to the treatment.

Presented herein, according to one aspect, are kits for treating a bowel disorder in a subject, comprising one or more actions for use.

Also presented herein, according to one aspect are packaged compositions comprising a therapeutically effective amount of one or more of a Form α, Form β, or Form γ polymorph of rifaximin and a pharmaceutically acceptable carrier or diluents, wherein the composition is formulated for treating a subject suffering from or susceptible to a bowel disorder, and packaged with instructions to treat a subject suffering from or susceptible to a bowel disorder.

Presented herein, according to another aspect, are processes for the production of one or more of a Form α, Form β, or Form γ polymorph of rifaximin, comprising:

reacting a molar equivalent of rifamycin O with an excess of 2-amino-4-methylpyridine in a solvent mixture comprising water and ethyl alcohol in volumetric ratios between 1:1 and 2:1 for a time between 2 and 8 hours;

treating the reaction mixture at room temperature with a solution of ascorbic acid in a mixture of water, ethyl alcohol and concentrated aqueous hydrochloric acid;

adjusting the pH of the solution to 2.0 with hydrochloric acid concentrated aqueous solution, filtering and washing the resulting solid with the same water/ethyl alcohol solvent mixture;

purifying the raw rifaximin by dissolution in ethyl alcohol;

precipitating rifaximin by addition of water, with between about 15% to about 70% to the weight amount of ethyl alcohol used for the dissolution at a temperature of from between about 50° C. to about 0° C. under stirring for between about 4 to about 36 hours;

filtering and washing a resulting solid with water; and drying the rifaximin at a temperature of from between about room temperature to about 105° C.

According to one embodiment, the drying is for Form α, Form β, or Form γ between about 2 hours and about 72 hours.

In one embodiment, the reacting a molar equivalent of rifamycin O with an excess of 2-amino-4-methylpyridine is at a temperature of from between about 40° C. to about 60° C.

In another embodiment, the purifying the raw rifaximin by dissolution in ethyl alcohol is at a temperature of from between about 45° C. to about 65° C.

According to one embodiment, the reacting a molar equivalent of rifamycin O with an excess of 2-amino-4-methylpyridine is from between about 2.0 to about 3.5 molar equivalents.

According to another embodiment, after precipitating rifaximin by addition of water, the method further comprises lowering the temperature to between about 28° C. to about 32° C. to start crystallization.

In one embodiment, the resulting suspension is kept at a temperature of from between about 40° C. to about 50° C. under stirring for a time from between about 6 to about 24 hours.

In one embodiment, the process further comprises cooling the suspension to about 0° C. for from between about 15 minutes and one hour; filtering the resulting solid; and drying the solid to a water content of lower than 4.5%, preferably from between 0% and about 3% water to form Form α.

According to another embodiment, after precipitating rifaximin by addition of water, the method further comprises:

cooling the solution to a temperature of from between about 28° C. to about 32° C.;

maintaining the solution at from between about 40° C. and 50° C. under stirring for between about 6 to about 24 hours;

cooling the solution to about 0° C. for between about 15 minutes to about one hour;

filtering a resulting solid;

drying the solid from between about 4.5 to about 40% water content to form Form β.

In one embodiment, after precipitating rifaximin by addition of water, the method further comprises:

cooling the solution to a temperature of from between about 28° C. to about 32° C.;

cooling the solution to about 0° C., under stirring, for between about 6 to about 24 hours;

filtering a resulting solid; and drying the sold to a water content of between 0% and about 2.0% to form Form γ.

Presented herein, according to one aspect, are methods for the production of rifaximin O, comprising:

reacting a molar equivalent of rifamycin O with an excess of 2-amino-4-methylpyridine in a solvent mixture comprising water and ethyl alcohol to form a reaction mixture;

treating the reaction mixture with a solution of a weak acid, water, and alcohol to lower the pH of the solution to form a suspension;

filtering the suspension and washing the resulting solid with a water, alcohol, and solvent mixture to form raw rifaximin;

purifying the raw rifaximin by dissolution in an alcohol at a temperature between 45° C. and 65° C.;

precipitating the raw rifaximin by the addition of water;

lowering of the temperature of the suspension to between about 50° C. to about 0° C. under stirring to form a second suspension;

filtering the second suspension; and washing a resulting solid with water and drying.

In one embodiment, the reacting a molar equivalent of rifamycin O with an excess of 2-amino-4-methylpyridine is from between about 2.0 to about 3.5 molar equivalents.

In another embodiment, the reacting a solvent mixture comprising water and ethyl alcohol is in volumetric ratios from between about 1:1 to about 2:1.

According to one embodiment, the alcohol is one or more of ethyl alcohol, menthol, propanol, or 2-butanol.

According to another embodiment, the reacting a solvent mixture comprising water and ethyl alcohol is for a time from between about 2 to about 8 hours.

In one embodiment, the reacting a solvent mixture comprising water and alcohol is at a temperature from between about 40° C. to about 60° C.

In one embodiment, the treating the reaction mixture is at about room temperature.

In one embodiment, the solution to treat the reaction mixture comprises a weak reducing agent in a mixture of water, alcohol and a strong acid.

In one embodiment, the weak reducing agent is one or more of ascorbic acid, sodium dithionate, or sodium thiosulphate.

In another embodiment, the strong acid is one or more of hydrochloric acid, sulphuric acid, or phosphoric acid.

According to one embodiment, when treating the reaction mixture the pH is lowered to about 2.0.

In one embodiment, the drying is by one or more of under vacuum, under conditions of normal pressure, or in the presence of a drying agent.

In another embodiment, the drying is at a temperature between about room temperature to about 105° C.

According to one embodiment, the drying is for a time from between about 2 to about 72 hours.

According to another embodiment, the precipitating the rifaximin is by the addition of water in weight amounts of from between about 15% to about 70% of the weight amount of ethyl alcohol used for the reacting.

According to one embodiment, the under stirring for a time from between about 4 to about 36 hours.

According to another embodiment, after the precipitation of raw rifaximin the method further comprises:

lowering the temperature to between about 28° C. to about 32° C.;

maintaining the temperature at between about 40° C. to about 50° C. under stirring for between about 6 to about 24 hours;

cooling to about 0° C. for between about 15 minutes to about one hour;

filtering a resulting solid; and drying the resulting solid to a water content from between about 3.0% to 0%, wherein the method forms Form α of rifaximin.

In one embodiment, after the precipitation of raw rifaximin the method further comprises:

lowering the temperature to between about 28° C. to about 32° C.;

maintaining the temperature at between about 40° C. to about 50° C. under stirring for between about 6 to about 24 hours;

cooling to about 0° C. for between about 15 minutes and about one hour;

filtering a resulting solid; and drying the solid to a water content greater than about 4.5% to form Form β of rifaximin.

According to one embodiment, after the precipitation of raw rifaximin the method further comprises:

lowering the temperature to between about 28° C. to about 32° C.;

cooling the temperature to about 0° C. under stirring for between about 6 to about 24 hours;

filtering a resulting solid; and drying the solid to a water content of between about 1.0% to about 2.0%, wherein the method produces Form γ of rifaximin.

BRIEF DESCRIPTION OF THE DRAWINGS

FIG. 1 is graphical depiction of the rate of dissolution of polymorphs α and β of rifaximin from 0 to 22 hours.

FIG. 2 is graphical depiction of the rate of dissolution of polymorphs α and β of rifaximin from 0-96 hours.

FIG. 3 is graphical depiction of the rate of dissolution of polymorphs β and γ of rifaximin from 0 to 22 hours.

FIG. 4 is graphical depiction of the rate of dissolution of polymorphs β and γ of rifaximin from 0-96 hours.

FIG. 5 is a table presenting the data obtained from the dissolution profiles depicted in FIGS. 1-4.

FIG. 6 is a table presenting data relating to the intrinsic dissolution rates of polymorph form β and γ of rifaximin.

DETAILED DESCRIPTION

Figure 7A:
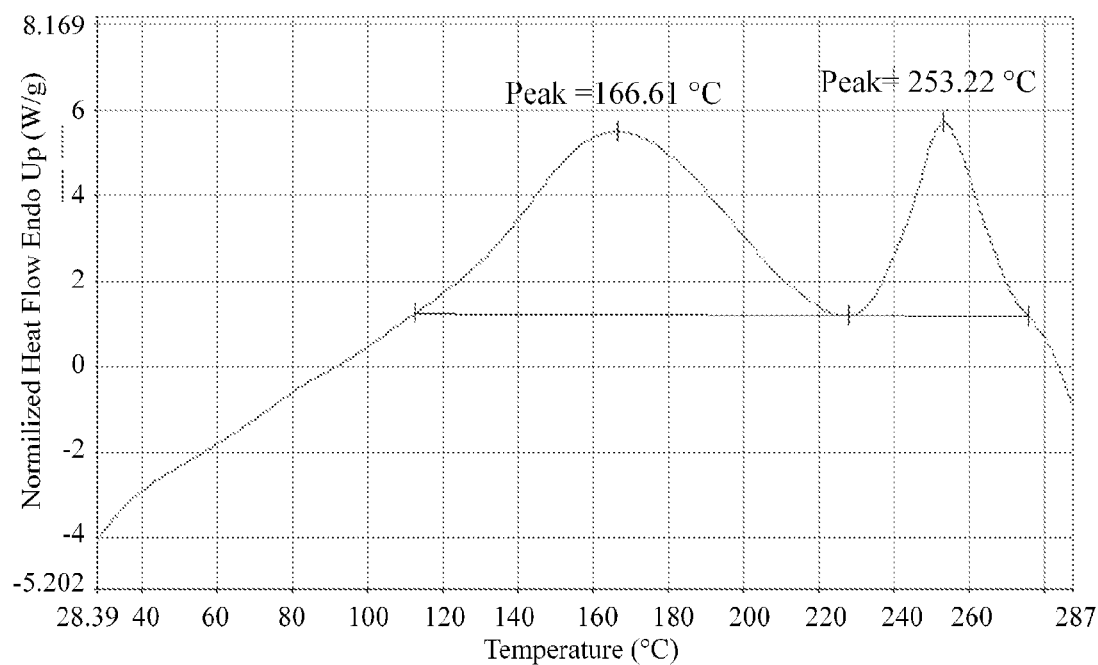
FIGS. 7a, b, and c graphically depict the differential scanning calorimetry (DSC) profile of polymorphous forms α, β, and γ of rifaximin, respectively.

The present invention relates to the use of forms α, β and γ of the antibiotic known as Rifaximin (INN), in the manufacture of medicinal preparations for the oral or topical route.

Rifaximin is a compound having the structure of formula I:

(I)

[Chemical structure of rifaximin]

As used herein, "rifaximin Form α," "Form α," "Form α of rifaximin," "polymorph α," and "rifaximin α" are used interchangeably to denote the polymorphic form of rifaximin as further described herein by, for example, one or more peaks of an x-ray diffractogram, differential scanning calorimetry data (FIG. 7a), dissolution (including intrinsic dissolution rates) (FIGS. 1 and 2) data and pharmacokinetic parameters. Form α comprises an x-ray powder diffraction pattern peak positions at about 7.4, 11.8 and 19.7 degrees 2-θ; or at about 6.6, 11.8, and 17.6 degrees 2-θ; or at about 7.4, 8.8, and 19.7 degrees 2-θ; or at about 7.9, 10.5 and 19.7 degrees 2-θ; or at about 6.6, 11.8 and 21.4 degrees 2-θ; or at about 7.9, 11.8 and 22.1; or at about 6.6, 7.4, 7.9, 8.8, 10.5, 11.8, 17.6, 18.5, 19.7, 21 and 22.1 degrees 2-θ and a water content between about 0 and about 4.5% (w/w), preferably between about 0 and 3.0% (w/w). Form α has a $C_{max}$ from about 0.0 ng/ml to about 10 ng/ml. Form α has a $t_{max}$ from about 1.0 h to about 6.0 h; an $AUC_{0-24h}$ between about 0 and about 100 ng·h/ml; and an $AUC_{0-inf}$ between about 10 and 24 ng·h/ml. Form α may be identified and characterized by one or more of these parameters and/or one or more of the peaks or points in the ranges.

As used herein, "rifaximin Form β," "Form β," "polymorph β," "Form β of rifaximin" and "rifaximin β" are used interchangeably to denote the polymorphic form of rifaximin as further described herein by, for example, one or more peaks of an x-ray diffractogram, intrinsic dissolution rates, data (FIGS. 1-6), differential scanning calorimetry (FIG. 7b), pharmacokinetic parameters (Table 1), and methods of making such form. Form β comprises x-ray powder diffraction pattern peak positions at about 5.4, 9.0, and 13.1 degrees 2-θ; or at about 6.4, 10.4 and 18.3 degrees 2-θ; or at about 7.8, 17.1 and 20.9 degrees 2-θ; or at about 7.8, 17.1 and 20.9 degrees 2-θ; at about 5.4, 7.8, 14.4 and 18.3 degrees 2-θ; or at about 5.4, 18.3, 20.9 degrees 2-θ; or at about 5.4, 6.4, 7.0, 7.8, 9, 10.4, 13.1, 14.4, 17.1, 17.9, 18.3, and 20.9 degrees 2-θ and a water content from about 4.5 to about 40%; a $C_{max}$ between about 0.0 and about 3.7 ng/ml; a $t_{max}$ between about 1.0 and about 6.0 h; an $AUC_{0-t}$ between about 0 and about 40 ng·h/ml; an $AUC_{0-inf}$ between about 0.0 ng·h/ml and about 50; and an intrinsic dissolution rate from about 0.001 to about 0.016 mg/min/cm². Form β may be identified and characterized by one or more of these parameters and/or one or more of the peaks or points in the ranges.

As used herein, "rifaximin Form γ," "Form γ," "polymorph γ," "Form γ of rifaximin" and "rifaximin γ" are used interchangeably to denote the polymorphic form of rifaximin as further described herein by, for example, one or more peaks of an x-ray diffractogram, dissolution (including intrinsic dissolution rates, FIGS. 3-6) data, differential scanning calorimetry data (FIG. 7c), pharmacokinetic parameters (Table 1), and methods of making such form. Form γ comprises identifying x-ray powder diffraction pattern peak positions at about 5.0; 7.1; 8.4 degrees 2-θ. Form γ has a water content from about 0% to about 2%; a $C_{max}$ from about 0.0 to about 5000 ng/ml; a $t_{max}$ from about 1.0 h to about 6.0 h; an $AUC_{0-24h}$ from 0.0 to about 22000 ng·h/ml and an intrinsic dissolution rate from about 0.1 to about 0.16 mg/min/cm². Form γ may be identified and characterized by one or more of these parameters and/or one or more of the peaks or points in the ranges.

As used herein, the term "about" when used in reference to x-ray powder diffraction pattern peak positions refers to the inherent variability of the peaks depending on, for example, the calibration of the equipment used, the process used to produce the polymorph, the age of the crystallized material and the like, depending on the instrumentation used. In this case the measure variability of the instrument was about ±0.2°. A person skilled in the art, having the benefit of this disclosure, would understand the use of "about" in this context. The term "about" in reference to other defined parameters, e.g., water content, $C_{max}$, $t_{max}$, AUC, intrinsic dissolution rates, temperature, and time, indicates the inherent variability in, for example, measuring the parameter or achieving the parameter. A person skilled in the art, having the benefit of this disclosure, would understand the variability of a parameter as connoted by the use of the word about.

Polymorphism, as used herein, refers to the occurrence of different crystalline forms of a single compound in distinct hydrate status, e.g., a property of some compounds and complexes. Thus, polymorphs are distinct solids sharing the same molecular formula, yet each polymorph may have distinct physical properties. Therefore, a single compound may give rise to a variety of polymorphic forms where each form has different and distinct physical properties, such as solubility profiles, melting point temperatures, hygroscopicity, particle shape, density, flowability, compactibility and/or x-ray diffraction peaks. The solubility of each polymorph may vary, thus, identifying the existence of pharmaceutical polymorphs is essential for providing pharmaceuticals with predicable solubility profiles. It is desirable to investigate all solid state forms of a drug, including all polymorphic forms, and to determine the stability, dissolution and flow properties of each polymorphic form. Polymorphic forms of a compound can be distinguished in a laboratory by X-ray diffraction spectroscopy and by other methods such as, infrared spectrometry. For a general review of polymorphs and the pharmaceutical applications of polymorphs see G. M. Wall, Pharm Manuf. 3, 33 (1986); J. K. Haleblian and W. McCrone, J. Pharm. Sci., 58, 911 (1969); and J. K. Haleblian, J. Pharm. Sci., 64, 1269 (1975), all of which are incorporated herein by reference.

As used herein, "subject" includes organisms which are capable of suffering from a bowel disorder or other disorder treatable by rifaximin or who could otherwise benefit from the administration of a polymorphic compound of the invention, such as human and non-human animals. Preferred human animals include human patients. The term "non-human animals" of the invention includes all vertebrates, e.g., mammals, e.g., rodents, e.g., mice, and non-mammals, such as non-human primates, e.g., sheep, dog, cow, chickens, amphibians, reptiles, etc. Susceptible to a bowel disorder is meant to include subjects at risk of developing a bowel disorder infection, i.e., subjects suffering from immune suppression, subjects that have been exposed to other subjects with a bacterial infection, physicians, nurses, subjects travelling to remote areas known to harbor bacteria that causes travellers' diarrhea, etc.

The language "a prophylactically effective amount" of a compound refers to an amount of a compound of the invention of formula (I) or otherwise described herein which is effective, upon single or multiple dose administration to the patient, in preventing or treating a bacterial infection.

The language "therapeutically effective amount" of a compound of the invention refers to an amount of an agent which is effective, upon single or multiple dose administration to the patient, in inhibiting the virus, or in prolonging the survivability of the patient with such a bacterial infection beyond that expected in the absence of such treatment.

Rifaximin exerts a broad antibacterial activity in the gastrointestinal tract against localized gastrointestinal bacteria that cause infectious diarrhea, including anaerobic strains. It has been reported that rifaximin is characterized by a negligible systemic absorption, due to its chemical and physical characteristics (Descombe J. J. et al. *Pharmacokinetic study of rifaximin after oral administration in healthy volunteers. Int J Clin Pharmacol Res,* 14 (2), 51-56, (1994)).

It has now been found that the level of systemic rifaximin adsorption can be modulated by administering distinct polymorphic forms of rifaximin, e.g., rifaximin Form α, rifaximin β and rifaximin γ. It is possible to have a difference in the adsorption of almost 5000 fold in the range from 0.001 to 1 μg/ml in blood depending on which polymorph is administered.

The differences in the bioavailability differentiate the pharmacological and toxicological behaviour of the polymorphic forms of rifaximin, e.g., α, β and γ. For example, rifaximin α and rifaximin β are negligibly absorbed through the oral route, while rifaximin γ shows a mild absorption. Rifaximin α and rifaximin β, which have little absorption, as shown herein in the examples, without wishing to be bound by any scientific theory, might act only through a topical action and have the advantage of very low toxicity. For example, oral administration of rifaximin α and rifaximin β would lead to topical action of the rifaximin in the gastro-intestinal tract with very low toxicity.

Rifaximin γ, which is mildly absorbed, may be advantageous for use against systemic micro-organisms, which are able to hide themselves and to partially elude the action of the topical antibiotics. Rifaximin γ, due to its solubility profile may also be useful to treat the upper GI tract. Thus, the administration of, for example, a combination of rifaximin polymorphs may be useful to treat upper and lower GI tract diseases.

In respect to possible adverse events coupled to the therapeutic use of rifaximin, the induction of bacterial resistance to the antibiotics is of particular relevance.

From this point of view, the difference found in the systemic absorption of the α, β and γ forms of rifaximin may be significant, because at sub-inhibitory concentration of rifaximin, such as in the range from 0.1 to 1 μg/ml, selection of resistant mutants has been demonstrated to be possible (Marchese A. et al. *In vitro activity of rifaximin, metronidazole and vancomycin against clostridium difficile and the rate of selection of spontaneously resistant mutants against representative anaerobic and aerobic bacteria, including ammonia-producing species. Chemotherapy,* 46(4), 253-266, (2000)).

The above-mentioned α, β and γ forms can be advantageously used as pure and homogeneous products in the manufacture of medicinal preparations containing rifaximin.

Bioavailability studies of the three polymorphs have been carried out on Beagle female dogs, by feeding them orally with a variable dose of rifaximin forms, collecting blood samples from the jugular vein of each animal before each dosing and 1, 2, 4, 6, 8 and 24 hours after each dosing, transferring the samples into tubes containing heparin and separating the plasma by centrifugation.

The experimental data reported in Example 13 and 14 are summarised in Table 1 wherein the range of values of $C_{max}$, $T_{max}$, $AUC_{0-24h}$, $AUC_{0-inf}$ are reported taking into account two standard deviations from the values obtained in Example 1 and 2. These ranges clearly show that rifaximin α and rifaximin β are negligibly absorbed, while rifaximin γ is absorbed at a value ($C_{max}$=1.085 μg/ml) comprised in the range of orders of magnitude from 0.01 to 1.0 μg/ml.

TABLE 1

Range of the Pharmacokinetic parameters for rifaximin polymorphs following a single oral administration of 100 mg/kg in the form of capsules to female dogs.

| Polymorphic form | $C_{max} \pm 2SD$ ng/mg | $t_{max}$ h | $AUC_{0-24h}$ ng.h/ml | $AUC_{0-inf}$ ng.h/mL |
|---|---|---|---|---|
| α | From 0.0 to 5.34 | From 1.0 to 6.0 | From 0.0 to 100 | From 0.0 to 110 |
| β | From 0.0 to 3.7 | From 1.0 to 6.0 | From 0.0 to 40 | From 0.0 to 50 |
| γ | From 0.0 to 5000 | From 1.0 to 6.0 | From 0.0 to 22000 | From 0.0 to 22000 |

Intrinsic dissolution tests were carried out on each of the three polymorphs according to the method described in the monograph 1087 at pages 2512-2513 of the USP (U.S. Pharmacopoeia) 27, clearly showing significant differences among rifaximin α, rifaximin β and rifaximin γ.

A sample of each rifaximin polymorph was put into a die and compressed at 5 tons by the punch of a hydraulic press to obtain a compacted pellet.

The die-holder containing the compacted pellet was then mounted on a laboratory stirring device, immersed in a dissolution medium and rotated by means of the stirring device.

The test, carried out in a dissolution medium made of aqueous phosphate buffer at ph 7.4 and of sodium lauryl sulfate at a temperature of 37±0.5° C., showed significant differences among the intrinsic dissolution rates exhibited by the three polymorphs. (FIGS. 1-3 graphically show the dissolution data while FIG. 5 is a chart of the data.) Rifaximin α has shown disintegration of the compacted pellet within 10 minutes, and it has not been possible to calculate the value of its intrinsic dissolution. The intrinsic dissolution of rifaximin γ is about ten times greater than that of rifaximin β in accordance with its bioavailability, which is more than hundred times greater than that of rifaximin β.

The above experimental results further point out the differences existing among the three rifaximin polymorphs.

Figure 7B:
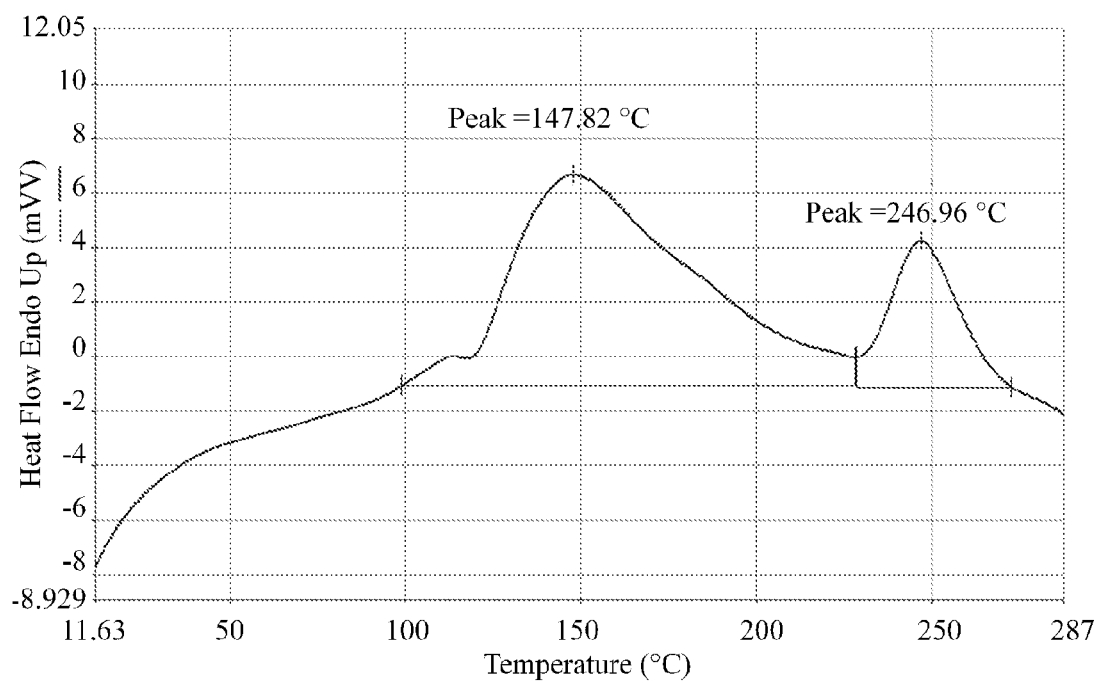
Figure 7C:
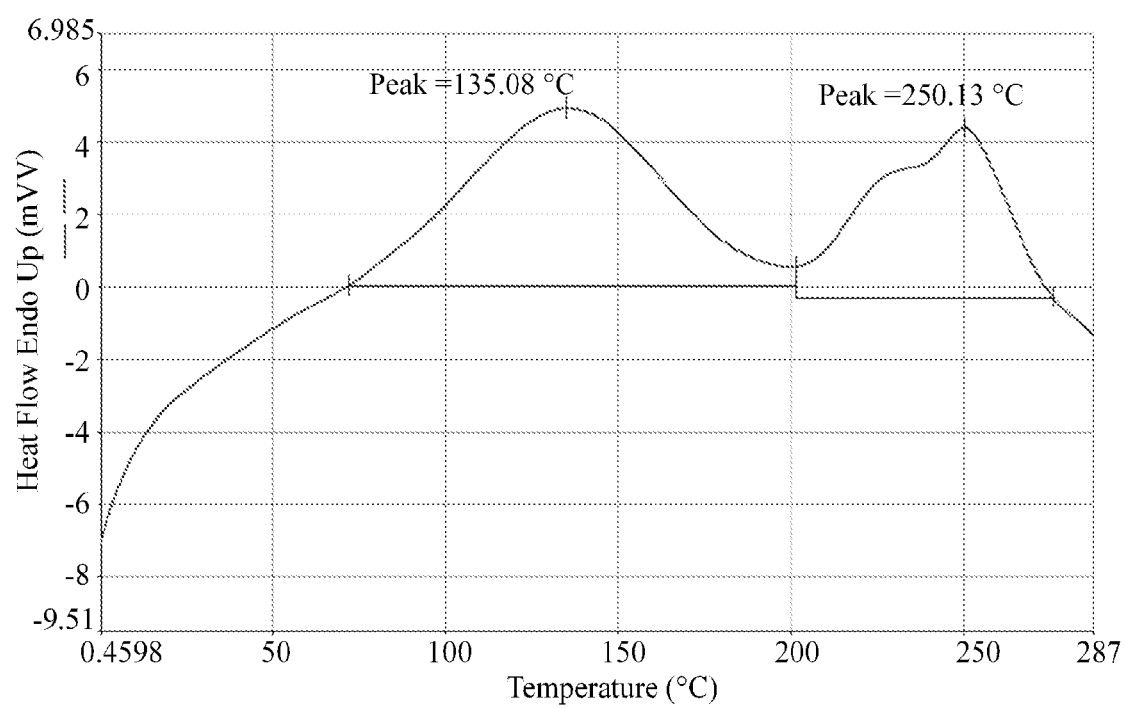

FIGS. 7a, 7b, 7c are the differential scanning calorimetry (DSC) profiles of polymorphs α, β, and γ.

Methods of Treatment

Provided herein are methods of treating, preventing, or alleviating bowel related disorders comprising administering to a subject in need thereof an effective amount of one or more of a Form α, Form β, or Form γ polymorph of rifaximin. Bowel related disorders include one or more of irritable bowel syndrome, diarrhea, microbe associated diarrhea, *Clostridium difficile* associated diarrhea, travellers' diarrhea, small intestinal bacterial overgrowth, Crohn's disease, chronic pancreatitis, pancreatic insufficiency, colitis, hepatic encephalopathy, or pouchitis.

The length of treatment for a particular bowel disorder will depend in part on the disorder. For example, travellers' diarrhea may only require treatment duration of 12 to about 72 hours, while Crohn's disease may require treatment durations from about 2 days to 3 months. Dosages of rifaximin will also vary depending on the diseases state. Proper dosage ranges are provided herein infra.

Provided herein are methods of treating or preventing a pathology in a patient suspected of being exposed to a biological warfare agent.

The identification of those patients who are in need of prophylactic treatment for bowel disorder is well within the ability and knowledge of one skilled in the art. Certain of the methods for identification of patients which are at risk of developing a bowel disorder which can be treated by the subject method are appreciated in the medical arts, such as family history, travel history and expected travel plans, the presence of risk factors associated with the development of that disease state in the subject patient. A clinician skilled in the art can readily identify such candidate patients, by the use of, for example, clinical tests, physical examination and medical/family/travel history.

A method of assessing the efficacy of the treatment in a subject includes determining the pre-treatment level of intestinal bacterial overgrowth by methods well known in the art (e.g., hydrogen breath testing, biopsy, sampling of the intestinal bacteria, etc.) and then administering a therapeutically effective amount of a rifaximin polymorph to the subject. After an appropriate period of time (e.g., after an initial period of treatment) from the administration of the compound, e.g., 2 hours, 4 hours, 8 hours, 12 hours, or 72 hours, the level of bacterial overgrowth is determined again. The modulation of the bacterial level indicates efficacy of the treatment. The level of bacterial overgrowth may be determined periodically throughout treatment. For example, the bacterial overgrowth may be checked every few hours, days or weeks to assess the further efficacy of the treatment. A decrease in bacterial overgrowth indicates that the treatment is efficacious. The method described may be used to screen or select patients that may benefit from treatment with a rifaximin polymorph.

In yet another aspect, a method of treating a subject suffering from or susceptible to a bowel disorder comprises administering to a subject in need thereof a therapeutically effective amount of a rifaximin polymorph described herein, to thereby treat the subject. Upon identification of a subject suffering from or susceptible to a bowel disorder, for example, IBS, one or more rifaximin polymorphs are administered.

In one aspect, methods of assessing the efficacy of treatment with a rifaximin polymorph in a subject comprise determining the pre-treatment level of bacterial overgrowth, administering a therapeutically effective amount of a rifaximin polymorph to the subject, and determining the bacterial overgrowth after an initial period of treatment with a rifaximin polymorph, wherein the modulation of the bacterial overgrowth indicates efficacy of an anti-bacterial treatment.

Efficacy of a treatment may be measured for example, as reduction of bacterial overgrowth. Efficacy may also be measured in terms of a reduction of symptoms associated with the bowel disorder, a stabilization of symptoms, or a cessation of symptoms associated with a bowel disorder, for example, a reduction of nausea, bloating, diarrhea, and the like.

In one aspect, methods of monitoring the progress of a subject being treated with a rifaximin polymorph comprise determining the pre-treatment level of bacterial overgrowth, administering a therapeutically effective amount of a rifaximin polymorph to the subject, and determining the bacterial overgrowth after an initial period of treatment with a rifaximin polymorph, wherein the modulation of the bacterial overgrowth indicates efficacy of an anti-bacterial treatment.

Pharmaceutical Preparations

The invention also provides pharmaceutical compositions, comprising an effective amount of a rifaximin polymorph (e.g., Form α, Form β, and/or Form γ) described herein and a pharmaceutically acceptable carrier. In a further embodiment, the effective amount is effective to treat a bacterial infection, e.g., small intestinal bacterial overgrowth, Crohn's disease, hepatic encephalopathy, antibiotic associated colitis, and/or diverticular disease.

For examples of the use of rifaximin to treat Travelers' diarrhea, see Infante R M, Ericsson C D, Zhi-Dong J, Ke S, Steffen R, Riopel L, Sack D A, DuPont, H L. Enteroaggregative *Escherichia coli* Diarrhea in Travelers: Response to Rifaximin Therapy. *Clinical Gastroenterology and Hepatology*. 2004; 2:135-138; and Steffen R, M.D., Sack D A, M.D., Riopel L, Ph.D., Zhi-Dong J, Ph.D., Sturchler M, M.D., Ericsson C D, M.D., Lowe B, M. Phil., Waiyaki P, Ph.D., White M, Ph.D., DuPont H L, M.D. Therapy of Travelers' Diarrhea With Rifaximin on Various Continents. *The American Journal of Gastroenterology*. May 2003, Volume 98, Number 5, all of which are incorporated herein by reference in their entirety.

The invention provides pharmaceutical compositions comprising one or more of a Form α, Form β, or Form γ polymorph of rifaximin and a pharmaceutically acceptable carrier. That is, formulations may contain only one polymorph or may contain a mixture of more than one polymorph. Mixtures may be selected, for example on the basis of desired amounts of systemic adsorption, dissolution profile, desired location in the digestive tract to be treated, and the like. The pharmaceutical composition further comprises excipients, for example, one or more of a diluting agent, binding agent, lubricating agent, disintegrating agent, coloring agent, flavouring agent or sweetening agent. Composition may be formulated for selected coated and uncoated tablets, hard and soft gelatin capsules, sugar-coated pills, lozenges, wafer sheets, pellets and powders in sealed packet. For example, compositions may be formulated for topical use, for example, ointments, pomades, creams, gels and lotions.

In an embodiment, the rifaximin polymorph is administered to the subject using a pharmaceutically-acceptable formulation, e.g., a pharmaceutically-acceptable formulation that provides sustained delivery of the rifaximin polymorph to a subject for at least 12 hours, 24 hours, 36 hours, 48 hours, one week, two weeks, three weeks, or four weeks after the pharmaceutically-acceptable formulation is administered to the subject.

In certain embodiments, these pharmaceutical compositions are suitable for topical or oral administration to a subject. In other embodiments, as described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes; (2) parenteral administration, for example, by subcutaneous, intramuscular or intravenous injection as, for example, a sterile solution or suspension; (3) topical application, for example, as a cream, ointment or spray applied to the skin; (4) intravaginally or intrarectally, for example, as a pessary, cream or foam; or (5) aerosol, for example, as an aqueous aerosol, liposomal preparation or solid particles containing the compound.

The phrase "pharmaceutically acceptable" refers to those rifaximin polymorphs of the present invention, compositions containing such compounds, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" includes pharmaceutically-acceptable material, composition or vehicle, such as a liquid or solid filler, diluent, excipient, solvent or encapsulating material, involved in carrying or transporting the subject chemical from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

Wetting agents, emulsifiers and lubricants, such as sodium lauryl sulfate and magnesium stearate, as well as coloring agents, release agents, coating agents, sweetening, flavouring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Compositions containing a rifaximin polymorph(s) include those suitable for oral, nasal, topical (including buccal and sublingual), rectal, vaginal, aerosol and/or parenteral administration. The compositions may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred %, this amount will range from about 1% to about ninety-nine % of active ingredient, preferably from about 5% to about 70%, most preferably from about 10% to about 30%.

Methods of preparing these compositions include the step of bringing into association a rifaximin polymorph(s) with the carrier and, optionally, one or more accessory ingredients. In general, the formulations are prepared by uniformly and intimately bringing into association a rifaximin polymorph with liquid carriers, or finely divided solid carriers, or both, and then, if necessary, shaping the product.

Compositions of the invention suitable for oral administration may be in the form of capsules, cachets, pills, tablets, lozenges (using a flavoured basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a rifaximin polymorph(s) as an active ingredient. A compound may also be administered as a bolus, electuary or paste.

The forms $\alpha$, $\beta$ and $\gamma$ can be advantageously used in the production of medicinal preparations having antibiotic activity, containing rifaximin, for both oral and topical use. The medicinal preparations for oral use will contain rifaximin $\alpha$ or $\beta$ or $\gamma$ together with the usual excipients, for example diluting agents such as mannitol, lactose and sorbitol; binding agents such as starches, gelatines, sugars, cellulose derivatives, natural gums and polyvinylpyrrolidone; lubricating agents such as talc, stearates, hydrogenated vegetable oils, polyethylenglycol and colloidal silicon dioxide; disintegrating agents such as starches, celluloses, alginates, gums and reticulated polymers; colouring, flavouring and sweetening agents.

The present invention relates to all of the solid preparations administrable by the oral route, for instance coated and uncoated tablets, of soft and hard gelatine capsules, sugar-coated pills, lozenges, wafer sheets, pellets and powders in sealed packets or other containers.

The medicinal preparations for topical use will contain rifaximin $\alpha$ or $\beta$ or $\gamma$ together with usual excipients, such as white petrolatum, white wax, lanoline and derivatives thereof, stearylic alcohol, propylene glycol, sodium lauryl sulfate, ethers of fatty polyoxyethylene alcohols, esters of fatty polyoxyethylene acids, sorbitan monostearate, glyceryl monostearate, propylene glycol monostearate, polyethylene glycols, methylcellulose, hydroxymethyl propylcellulose, sodium carboxymethylcellulose, colloidal aluminium and magnesium silicate, sodium alginate.

The present invention relates to all of the topical preparations, for instance ointments, pomades, creams, gels and lotions.

In solid dosage forms of the invention for oral administration (capsules, tablets, pills, dragees, powders, granules and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such as talc, calcium stearate, magnesium stearate, solid polyethylene glycols, sodium lauryl sulfate, and mixtures thereof; and (10) colouring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered active ingredient moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the rifaximin polymorph(s) include pharmaceutically-acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

In addition to inert diluents, the oral compositions can include adjuvants such as wetting agents, emulsifying and suspending agents, sweetening, flavoring, coloring, perfuming and preservative agents.

Suspensions, in addition to the active rifaximin polymorph(s) may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Pharmaceutical compositions of the invention for rectal or vaginal administration may be presented as a suppository, which may be prepared by mixing one or more rifaximin polymorph(s) with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active agent.

Compositions of the present invention which are suitable for vaginal administration also include pessaries, tampons, creams, gels, pastes, foams or spray formulations containing such carriers as are known in the art to be appropriate.

Dosage forms for the topical or transdermal administration of a rifaximin polymorph(s) include powders, sprays, ointments, pastes, creams, lotions, gels, solutions, patches and inhalants. The active rifaximin polymorph(s) may be mixed under sterile conditions with a pharmaceutically-acceptable carrier, and with any preservatives, buffers, or propellants which may be required.

The ointments, pastes, creams and gels may contain, in addition to rifaximin polymorph(s) of the present invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a rifaximin polymorph(s), excipients such as lactose, talc, silicic acid, aluminium hydroxide, calcium silicates and polyamide powder, or mixtures of these substances. Sprays can additionally contain customary propellants, such as chlorofluorohydrocarbons and volatile unsubstituted hydrocarbons, such as butane and propane.

The rifaximin polymorph(s) can be alternatively administered by aerosol. This is accomplished by preparing an aqueous aerosol, liposomal preparation or solid particles containing the compound. A non-aqueous (e.g., fluorocarbon propellant) suspension could be used. Sonic nebulizers are preferred because they minimize exposing the agent to shear, which can result in degradation of the compound.

Ordinarily, an aqueous aerosol is made by formulating an aqueous solution or suspension of the agent together with conventional pharmaceutically-acceptable carriers and stabilizers. The carriers and stabilizers vary with the requirements of the particular compound, but typically include non-ionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Transdermal patches have the added advantage of providing controlled delivery of a rifaximin polymorph(s) to the body. Such dosage forms can be made by dissolving or dispersing the agent in the proper medium. Absorption enhancers can also be used to increase the flux of the active ingredient across the skin. The rate of such flux can be controlled by either providing a rate controlling membrane or dispersing the active ingredient in a polymer matrix or gel.

Ophthalmic formulations, eye ointments, powders, solutions and the like, are also contemplated as being within the scope of the invention.

Pharmaceutical compositions of the invention suitable for parenteral administration comprise one or more rifaximin polymorph(s) in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and non-aqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of rifaximin polymorph(s) in biodegradable polymers such as polylactide-polyglycolide. Depending on the ratio of drug to polymer, and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissue.

When the rifaximin polymorph(s) are administered as pharmaceuticals, to humans and animals, they can be given per se or as a pharmaceutical composition containing, for example, 0.1 to 99.5% (more preferably, 0.5 to 90%) of active ingredient in combination with a pharmaceutically-acceptable carrier.

Regardless of the route of administration selected, the rifaximin polymorph(s), which may be used in a suitable hydrated form, and/or the pharmaceutical compositions of the present invention, are formulated into pharmaceutically-acceptable dosage forms by conventional methods known to those of skill in the art.

Actual dosage levels and time course of administration of the active ingredients in the pharmaceutical compositions of the invention may be varied so as to obtain an amount of the active ingredient which is effective to achieve the desired therapeutic response for a particular patient, composition, and mode of administration, without being toxic to the patient. An exemplary dose range is from 100 to 1800 mg per day.

A preferred dose of the rifaximin polymorph for the present invention is the maximum that a patient can tolerate without developing serious side effects. Preferably, the rifaximin polymorph of the present invention is administered at a concentration of about 1 mg to about 200 mg per kilogram of body weight, about 10—about 100 mg/kg or about 40 mg—about 80 mg/kg of body weight. Ranges intermediate to the above-recited values are also intended to be part of the invention.

In combination therapy treatment, both the compounds of this invention and the other drug agent(s) are administered to mammals (e.g., humans, male or female) by conventional methods. The agents may be administered in a single dosage form or in separate dosage forms. Effective amounts of the other therapeutic agents are well known to those skilled in the art. However, it is well within the skilled artisan's purview to determine the other therapeutic agent's optimal effective-amount range. In one embodiment of the invention in which another therapeutic agent is administered to an animal, the effective amount of the compound of this invention is less than its effective amount in case the other therapeutic agent is not administered. In another embodiment, the effective amount of the conventional agent is less than its effective amount in case the compound of this invention is not administered. In this way, undesired side effects associated with high doses of either agent may be minimized. Other potential advantages (including without limitation improved dosing regimens and/or reduced drug cost) will be apparent to those skilled in the art.

In various embodiments, the therapies (e.g., prophylactic or therapeutic agents) are administered less than 5 minutes apart, less than 30 minutes apart, 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours part. In preferred embodiments, two or more therapies are administered within the same patient's visit.

In certain embodiments, one or more compounds of the invention and one or more other therapies (e.g., prophylactic or therapeutic agents) are cyclically administered. Cycling therapy involves the administration of a first therapy (e.g., a first prophylactic or therapeutic agent) for a period of time, followed by the administration of a second therapy (e.g., a second prophylactic or therapeutic agent) for a period of time, optionally, followed by the administration of a third therapy (e.g., prophylactic or therapeutic agent) for a period of time and so forth, and repeating this sequential administration, i.e., the cycle in order to reduce the development of resistance to one of the therapies, to avoid or reduce the side effects of one of the therapies, and/or to improve the efficacy of the therapies.

In certain embodiments, the administration of the same compounds of the invention may be repeated and the administrations may be separated by at least 1 day, 2 days, 3 days, 5 days, 10 days, 15 days, 30 days, 45 days, 2 months, 75 days, 3 months, or at least 6 months. In other embodiments, the administration of the same therapy (e.g., prophylactic or therapeutic agent) other than a rifaximin polymorph may be repeated and the administration may be separated by at least at least 1 day, 2 days, 3 days, 5 days, 10 days, 15 days, 30 days, 45 days, 2 months, 75 days, 3 months, or at least 6 months.

Certain indications may require longer treatment times. For example, travellers' diarrhea treatment may only last from between about 12 hours to about 72 hours, while a treatment for Crohn's disease may be from between about 1 day to about 3 months.

Kits are also provided herein, for example, kits for treating a bowel disorder in a subject. The kits may contain, for example, one or more of a Form α, Form β, or Form γ polymorph of rifaximin and instructions for use. The instructions for use may contain prescribing information, dosage information, storage information, and the like.

Packaged compositions are also provided, and may comprise a therapeutically effective amount of one or more of a Form α, Form β, or Form γ polymorph of rifaximin and a pharmaceutically acceptable carrier or diluent, wherein the composition is formulated for treating a subject suffering from or susceptible to a bowel disorder, and packaged with instructions to treat a subject suffering from or susceptible to a bowel disorder.

EXAMPLES

Example 1

Preparation of Raw Rifaximin and of Dried Raw Rifaximin

In a three-necked flask equipped with mechanic stirrer, thermometer and reflux condenser, 120 ml of demineralized water, 96 ml of ethyl alcohol, 63.5 g of rifamycin O and 27.2 g of 2-amino-4-methylpyridine are loaded in succession at room temperature. After loading, the mass is heated at 47±3° C. and kept under stirring at this temperature for 5 hours, then is cooled to 20±3° C. and, during 30 minutes, is added with a mixture, prepared separately, of 9 ml of demineralized water, 12.6 ml of ethyl alcohol, 1.68 g of ascorbic acid and 9.28 g of aqueous concentrated hydrochloric acid. After completion of the addition, the mass is kept under stirring for 30 minutes at an inner temperature of 20±3° C. then 7.72 g of concentrated hydrochloric acid are dripped until a pH equal to 2.0, while keeping said temperature.

After completion of the addition, the mass is kept under stirring for 30 minutes, keeping an inner temperature of 20° C., then the precipitate is filtered and washed with a mixture of 32 ml of demineralized water and of 25 ml of ethyl alcohol. The resulting "raw rifaximin" (89.2 g) is dried under vacuum at room temperature for 12 hours obtaining 64.4 g of "dried raw rifaximin" which shows a water content of 5.6% and a diffractogram corresponding to the polymorphic form β. The product is further dried under vacuum until constant weight to afford 62.2 g of dried raw rifaximin having a water content of 2.2%, whose diffractogram corresponds to the polymorphic form α.

The product is hygroscopic and the obtained polymorphic form is reversible: the polymorphic form α absorbs water from atmospheric humidity, depending on the relative humidity and the exposure time. When the water content absorbed by the polymorphic form α becomes higher than 4.5%, polymorphous α converts to polymorphous β. This in its turn loses part of water by drying, changing into the polymorphic form α when a water content between 3.% and 0% is reached.

Example 2

Preparation of Rifaximin γ

163 ml of ethyl alcohol and 62.2 g of dried raw rifaximin are loaded at room temperature into a three-necked flask equipped with mechanic stirrer, thermometer and reflux condenser. The suspension is heated at 57±3° C. under stirring until complete dissolution of the solid, and added with 70 ml of demineralized water at this temperature in 30 minutes. After completion of the addition the temperature is brought to 30° C. in 40 minutes and kept at this value until complete crystallization, then the temperature is further lowered to 0° C. in 2 hours and kept at this value for 6 hours. The suspension is then filtered and the solid is washed with 180 g of demineralized water and dried under vacuum at room temperature until constant weight, thereby obtaining 52.7 g of pure rifaximin γ having water content of 1.5%.

The form γ is characterised by a powder X-ray diffractogram showing significant peaks at diffraction angles 2θ of 5.0°; 7.1°; 8.4°.

Example 3

Preparation of Rifaximin α

62.2 grams of dried raw rifaximin and 163 ml of ethyl alcohol are loaded at room temperature into a three-necked flask equipped with mechanic stirrer, thermometer and reflux condenser. The suspension is heated at 57±3° C. until complete dissolution of the solid and then 70 ml of demineralized water are added at this temperature during 30 minutes. After completion of the addition, the temperature is brought to 30° C. during 40 minutes and is kept at this value until plentiful crystallization. The temperature of the suspension is then brought to about 40° C. and kept at this value during 20 hours under stirring; then the temperature is decreased to 0° C. in 30 minutes and the suspension is immediately filtered. The solid is washed with 180 ml of demineralized water and dried under vacuum at room temperature until constant weight, thereby obtaining 51.9 g of rifaximin form α with a water content equal to 2.5% and a powder X-ray diffractogram showing peaks at values of angles 2θ of 6.6°; 7.4°; 7.9°; 8.8°; 10.5°; 11.1°; 11.8°; 12.9°; 17.6°; 18.5°; 19.7°; 21.0°; 21.4°; 22.1°.

Example 4

Preparation of Rifaximin α

89.2 grams of raw rifaximin and 170 ml of ethyl alcohol are loaded at room temperature into a three-necked flask equipped with mechanic stirrer, thermometer and reflux condenser, then the suspension is heated at 57±3° C. until complete dissolution of the solid. The temperature is brought to 50° C. and then 51.7 ml of demineralized water are added at this temperature during 30 minutes. After completion of the addition the temperature is brought to 30° C. in one hour and the suspension is kept for 30 minutes at this temperature obtaining a plentiful crystallization. The temperature of the suspension is brought to 40° C. and kept at this value during 20 hours under stirring and then further lowered to 0° C. during 30 minutes after which the suspension is immediately filtered. The solid is washed with 240 ml of demineralized water and dried under vacuum at 65° C. until constant weight thereby obtaining 46.7 g of rifaximin α with a water content equal to 2.5%.

Example 5

Preparation of Rifaximin α

Example 3 is repeated, but increasing to 50° C. the temperature at which the suspension is kept and lowering to 7 hours the time in which the suspension is kept at this temperature. The product obtained is equal to that of example 3.

Example 6

Preparation of Rifaximin β

The crystallization of the dried raw rifaximin is carried out according to the process described in example 3. Drying under vacuum at room temperature is monitored by Karl Fischer and stopped when the water content reaches 5.0%: 52.6 g of rifaximin β are obtained characterised by a powder X-ray diffractogram showing peaks at values of angles 2θ of 5.4°; 6.4°; 7.0°; 7.8°; 9.0°; 10.4°; 13.1°, 14.4°; 17.1°; 17.9°; 18.3°; 20.9°.

Example 7

Preparation of Rifaximin α Starting from Rifaximin γ

5 grams of rifaximin γ are suspended in a mixture of 13 ml of ethyl alcohol and 5.6 ml of water and the suspension is heated at 40° C. during 24 hours under stirring in a 50 ml flask equipped with condenser, thermometer and mechanic stirrer.

The suspension is then filtered and the solid is washed with water, then dried under vacuum at room temperature until constant weight. 4 grams of rifaximin are obtained showing a powder X-ray diffractogram corresponding to that of the polymorphic form α and a water content equal to 2.6%.

Example 8

Preparation of Rifaximin γ Starting from Rifaximin α

15 grams of rifaximin form α and 52.4 ml of ethyl alcohol are loaded into a 250 ml three-necked flask equipped with reflux condenser, thermometer and mechanical stirrer; the suspension is heated under stirring at the temperature of 50° C. until complete dissolution of the solid.

The clear solution is added with 22.5 ml of water in 30 minutes under stirring, cooled to 30° C. and kept at this temperature for 30 minutes. The formed suspension is cooled to 0° C. under strong stirring and kept at this temperature during 6 hours. After this time, part of the suspension is taken, filtered, washed with demineralized water and dried under vacuum at 30° C. until constant weight.

The resulting product, 3.7 g, shows a diffractogram consistent with that of the form γ and a water content of 1.7%.

The remaining part of the suspension is kept at 0° C. for further 18 hours under strong stirring and then is filtered, washed with demineralized water and dried at 30° C. under vacuum until constant weight. 9 grams of product showing a diffractogram consistent with that of the form γ and a water content equal to 1.6% are obtained.

Example 9

Preparation of Rifaximin α Starting from Rifaximin β

5 grams of rifaximin β having a water content equal to 5.0% are dried under vacuum at +30° C. during 8 hours obtaining 4.85 g of rifaximin α having a water content equal to 2.3%.

Example 10

Preparation of Rifaximin β Starting from Rifaximin α

5 grams of rifaximin α having a water content equal to 2.5% are kept during 40 hours in an atmosphere containing a relative humidity equal to 56% made by means of a saturated aqueous solution of calcium nitrate tetrahydrate. 5.17 grams of rifaximin β with a water content equal to 5.9% are obtained after this time.

Example 11

Preparation of Rifaximin β Starting from Rifaximin α

10 grams of rifaximin α having a water content equal to 2.5% are humidified by sprayed water. 11 grams of rifaximin β with a water content equal to 12.3% are obtained.

Example 12

Preparation of Rifaximin β Starting from Rifaximin α

10 grams of rifaximin α having a water content equal to 3.0% are humidified by sprayed water. 13.35 grams of rifaximin β with a water content equal to 36.5% are obtained.

Example 13

Bioavailability in Dogs by Oral Route Using Different Polymorphic Forms of Rifaximin Twelve 20 week pure-bred Beagle female dogs weighing between 5.0 and 7.5 kg, have been divided into three groups of four dogs.

The first of these three groups has been treated with rifaximin α, the second with rifaximin β and third with rifaximin γ according to the following procedure.

Each dog received orally 100 mg/kg of one of the rifaximin polymorphs in gelatin capsules and 2 ml blood samples were collected from the jugular vein of each animal before each administration and 1, 2, 4, 6, 8 and 24 hours after the administration. Each sample was transferred into an heparinized tube and was centrifuged; the plasma was divided into two 500 µl aliquots and frozen at −20° C.

The rifaximin contained in the plasma was assayed by means of the validated LC-MS/MS method and the following parameters were calculated according to standard non-compartmental analysis:

$C_{max}$=maximum plasma concentration of rifaximin observed in the plasma;

$T_{max}$=time at which the $C_{max}$ is reached;

AUC=area under the concentration-time curve calculated through the linear trapezoidal rule.

The results reported in the following table 2 clearly show how the rifaximin γ is very much more absorbed, more than $10^2$ times, in respect of rifaximin α and rifaximin β which are practically not absorbed.

TABLE 2

Pharmacokinetic parameters for rifaximin polymorphs following single oral administration of 100 mg/kg in the form of capsules to female dogs.

| Polymorphic form | $C_{max}$ ng/ml | $t_{max}$ h | $AUC_{0-24h}$ ng.h/ml | $AUC_{0-inf}$ ng.h/mL |
|---|---|---|---|---|
| α | 2.631 ± 0.7 | 4 | 17 ± 7 | 17 ± 7 |
| β | 1.096 ± 0.6 | 4 | 10 ± 7 | 12 ± 8 |
| γ | 1085.1 ± 878.69 | 2.25 | 4795 ± 4120 | 4894 ± 4107 |

Example 14

Bioavailability in Dogs by Oral Route Using Rifaximin Form γ in Comparison to Rifaximin Form α

In this experiment the Rifaximin form γ was administered at the doses of 25, 100 and 300 mg/kg to dogs in comparison with 100 mg/kg of polymorph α.

Sixteen 20 week pure-bred Beagle female dogs weighing between 5.0 and 7.5 kg, have been divided into four groups of four dogs.

The first of these four groups has been treated with rifaximin α, the second, third and fourth with rifaximin γ respectively at a dosage of 25 mg/kg, 50 mg/kg and 100 mg/Kg.

Each dog received orally 100 mg/kg of one of the rifaximin polymorphs in gelatin capsules and 2 ml blood samples were collected from the jugular vein of each animal before each administration and 1, 2, 4, 6, 8 and 24 hours after the administration. Each sample was transferred into a heparinized tube and was centrifuged; the plasma was divided into 500 µl two aliquots and frozen at −20° C.

The rifaximin contained in the plasma was assayed by means of the validated LC-MS/MS method and the following parameters were calculated according to standard non-compartmental analysis:

$C_{max}$=maximum plasma concentration of rifaximin observed in the plasma;

$T_{max}$=time at which the $C_{max}$ is reached;

AUC=area under the concentration-time curve calculated through the linear trapezoidal rule.

Following administration of polymorph γ at three different dose levels, the exposure in terms of AUC and $C_{max}$ increased with increasing dose, but more than proportionally. In fact, for a dose increment of 4-fold (from 25 to 100 mg/kg), 3-fold (from 100 to 300 mg/kg) there was a 8.8 and 9.3-fold increase in AUC and 11 and 2.5-fold increase in $C_{max}$.

The total systemic exposure of rifaximin, in terms of mean AUC, showed a higher bioavailability at 100 mg/kg of polymorph γ (AUC was 2693 ng·h/mL), when compared to 100 mg/kg of polymorph α (AUC was 37 ng·h/mL), confirming the results of the previous experiment.

With respect to dose dependency, after single oral administration of Rifaximin polymorph γ, exposure in the female dogs tended to increase in an over-proportional way compared to the administered dose.

The data are reported in the following table 3.

TABLE 3

Pharmacokinetic parameters for rifaximin polymorph γ following different oral administration of capsules to female dogs.

| Treatment (mg/mg) | Polymorphic form | $C_{max}$ ng/ml | $t_{max}$ h | $AUC_{0-24h}$ ng.h/ml | $AUC_{0-inf}$ ng.h/mL |
|---|---|---|---|---|---|
| 100 | α | 7.24 | 2.5 | 37 | 37 |
| 25 | γ | 114.01 | 1.5 | 304 | 548 |
| 100 | γ | 1268.80 | 2 | 2693 | 2937 |
| 300 | γ | 3145.68 | 3 | 25030 | 25513 |

Example 15

Intrinsic Dissolution Test

A sample of 100 mg of each rifaximin polymorph was submitted to the intrinsic dissolution test carried out as described in the monograph 1087 at pages 2512-2513 of the USP (U.S. Pharmacopoeia) 27.

100 Milligrams of a rifaximin polymorphs were put into a die and compressed for 1 minute under a pressure of 5 tons by means of a punch in a hydraulic press.

A compacted pellet was formed in the die with a single face of defined area exposed on the bottom of the die so that from 50% to 75% of the compacted pellet could dissolve in an appropriate dissolution medium.

The holder containing the die was mounted on a laboratory stirring device, immersed in a glass vessel containing a dissolution medium and rotated at a rotation speed of 100 rpm by means of the stirring device, while keeping the temperature of the dissolution medium at 37±0.5° C. The dissolution medium contained in the glass vessel consisted of 1000 ml of 0.1M aqueous phosphate buffer pH 7.4 containing 4.5 g of sodium lauryl sulphate (SLS) and was kept at 37±0.5° C. for the whole duration of the test.

Samples of 2 ml of solution were taken after 15, 30, 45 and 60 minutes from the start of the dissolution procedure and analysed by HPLC for the amount of rifaximin dissolved.

The sample containing rifaximin α systematically showed disintegration of the compacted pellet within 10 minutes and said phenomenon was also present at lower concentrations (0.1% and 0.3%) of sodium lauryl sulphate and even in the absence of said surfactant, so that the value of its intrinsic dissolution could not be calculated.

The intrinsic dissolution of rifaximin γ was about ten times as much that of rifaximin β at every time, as it can be inferred by the experimental results shown in the following Table 4.

TABLE 4

Intrinsic dissolution in 0.1M aqueous phosphate buffer pH 7.4 with 0.45% sodium lauryl sulphate

| | Rifaximin dissolved (mg/cm$^2$) | |
|---|---|---|
| Time (min) | β polymorph | γ polymorph |
| 15 | 0.28 | 2.46 |
| 30 | 0.50 | 4.52 |
| 45 | 0.72 | 6.44 |
| 60 | 0.94 | 9.04 |
| Intrinsic dissolution rate (mg/min/cm$^2$) | 0.0147 | 0.1444 |

Only the results for β and γ forms are reported, since systematically form α showed disintegration within 10 minutes. This phenomenon was present at different concentrations of SLS (0.1%, 0.3% and 0.45%) and also in the absence of SLS.

What is claimed is:

1. A method of preparing a pharmaceutical composition having controlled systemic absorption of rifaximin, said method comprising combining two or more polymorphs of rifaximin selected from the group consisting of Form α, Form β, and Form γ wherein the amount of absorption of said rifaximin is modulated by adjusting the relative proportions of Form α, Form β, and Form γ rifaximin to form a mixture of rifaximin polymorphs and combining the mixture with a pharmaceutically acceptable excipient or carrier,
   wherein the rifaximin Form α has x-ray powder diffraction pattern peaks at about 7.4°; 19.7°; 21.0° and 22,1° 2-θ,
   wherein the rifaximin Form β has x-ray powder diffraction pattern peaks at about 5.4°; 9.0°; and 20.9° 2-θ, and
   wherein the rifaximin Form γ has x-ray powder diffraction pattern peaks at about 5.0°, 7.1°, and 8.4° 2-θ, 2. A method of preparing a pharmaceutical composition, said method comprising selecting a mixture of two or more rifaximin polymorphs, wherein said two or more rifaximin polymorphs are two or more of Form α, Form β, and Form γ, and combining a therapeutically effective amount of said mixture with a pharmaceutically acceptable excipient or carrier, wherein the rifaximin Of the obtained pharmaceutical composition has a controlled systemic absorption determined by the relative proportions of and Form α, Form β, Form γ rifaximin, and
   wherein the rifaximin Form α has x-ray powder diffraction pattern peaks at about 7.4°; 19.7°; 21.0° and 22.1° 2-θ,
   wherein the rifaximin Form β has x-ray powder diffraction pattern peaks at about 5.4° ; 9.0° ; and 20.9° 2-θ; and
   wherein the rifaximin Form γ has x-ray powder diffraction pattern peaks at about 5.0° , 7.1°, and 8.4° 2-θ.

3. The method of claim 2, wherein when rifaximin Form α is present, rifaximin Form α is characterized as having water content of less than 4.5%; wherein when rifaximin Form β is present, rifaximin Form β is characterized as having a water content of greater than or equal to 4.5%; and wherein when rifaximin Form γ is present, rifaximin Form γ is characterized as having a water content from about 0% to about 2%.

4. The method of claim 3, wherein the rifaximin Form α as a water content of between 0% and about 3%.

5. The method of claim 3, wherein the rifaximin Form β has a water content between about 4.5% to about 40%.

6. The method of claim 3, wherein the rifaximin Form β has a dissolution rate of from about 0.001 to about 0.016 mg/min/cm$^2$.

7. The method of claim 3, wherein the rifaximin Form γ has a dissolution rate of from about 0.1 to about 0.16 mg/min/cm².

8. The method of claim 2, wherein the excipient is one or more of a diluting agent, binding agent, lubricating agent, disintegrating agent, absorption accelerating agents, wetting agents, absorbents, coloring agent, flavoring agent or sweetening agent.

9. The method of claim 8, wherein the pharmaceutical composition is formulated as liquid preparation.

10. The method of claim 8, wherein the pharmaceutical composition is formulated as topical preparation.

11. The method of claim 8, wherein the pharmaceutical composition is formulated as a preparation administrable by oral, rectal or vaginal route.

12. The method of claim 10, wherein the pharmaceutical composition is a solid dosage form.

13. The method of claim 11, wherein said solid dosage form is selected from among capsules, tablets, pills, dragees, powders and granules.

14. The method of claim 12, wherein said solid dosage form is administrable by an oral route and wherein said solid dosage form is selected from among coated tablets, uncoated tablets, soft gelatin capsules, hard gelatin capsules, sugar-coated tablets, lozenges, wafer sheets, pellets and powders in sealed containers.

15. The method of claim 13, wherein the pharmaceutical composition is formulated for treating a subject suffering from or susceptible to a bowel disorder and packaged with instructions to treat a subject suffering from or susceptible to a bowel disorder.

* * * * *